US009827132B2

(12) United States Patent
Mueller et al.

(10) Patent No.: US 9,827,132 B2
(45) Date of Patent: *Nov. 28, 2017

(54) ELBOW BRACE

(71) Applicant: Mueller Sports Medicine, Inc., Prairie du Sac, WI (US)

(72) Inventors: Brett Mueller, Middleton, WI (US); Zhaodong Max Li, Lodi, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 413 days.

This patent is subject to a terminal disclaimer.

(21) Appl. No.: 14/293,145

(22) Filed: Jun. 2, 2014

(65) Prior Publication Data

US 2014/0358055 A1   Dec. 4, 2014

Related U.S. Application Data

(60) Provisional application No. 61/829,248, filed on May 31, 2013.

(51) Int. Cl.
*A61F 5/058* (2006.01)
*A61F 5/01* (2006.01)

(52) U.S. Cl.
CPC .................. *A61F 5/0118* (2013.01)

(58) Field of Classification Search
CPC .... A61F 5/0104; A61F 5/0106; A61F 5/0109; A61F 5/0118; A61F 5/0123; A61F 5/013; A41D 13/055; A41D 13/0562; A41D 13/0568; A41D 13/06; A41D 13/065; A41D 13/08
See application file for complete search history.

(56) References Cited

U.S. PATENT DOCUMENTS

| | | | | |
|---|---|---|---|---|
| 5,024,216 | A | * 6/1991 | Shiono | A61F 5/0123 2/24 |
| 5,472,413 | A | * 12/1995 | Detty | A61F 5/0104 2/16 |
| 5,865,777 | A | 2/1999 | Detty | |
| 6,238,360 | B1 | 5/2001 | Gildersleeve | |
| 9,254,215 | B2 | * 2/2016 | Mueller | A61F 5/0109 |
| 2008/0255494 | A1 | * 10/2008 | Rousso | A61F 13/06 602/62 |
| 2011/0066095 | A1 | 3/2011 | Price | |

FOREIGN PATENT DOCUMENTS

WO   WO2005/120500 A2   12/2005

* cited by examiner

*Primary Examiner* — Kari Rodriquez
(74) *Attorney, Agent, or Firm* — Rick L. Abegglen

(57) ABSTRACT

An elbow brace for use by athletes or others requiring protection and support of the elbow. The elbow brace includes a base and a tension member. The base is comprised of elastic material and configured to closely fit around the elbow. A tension member having upper and lower pairs of tensioning straps is fastened to the interior surface of the base, with the tensioning straps extending through upper and lower apertures in the base for detachable attachment to the exterior surface of the base. The tension member may include an anchor portion made of material that stretches in multiple directions, and strap portions that stretch primarily lengthwise.

4 Claims, 15 Drawing Sheets

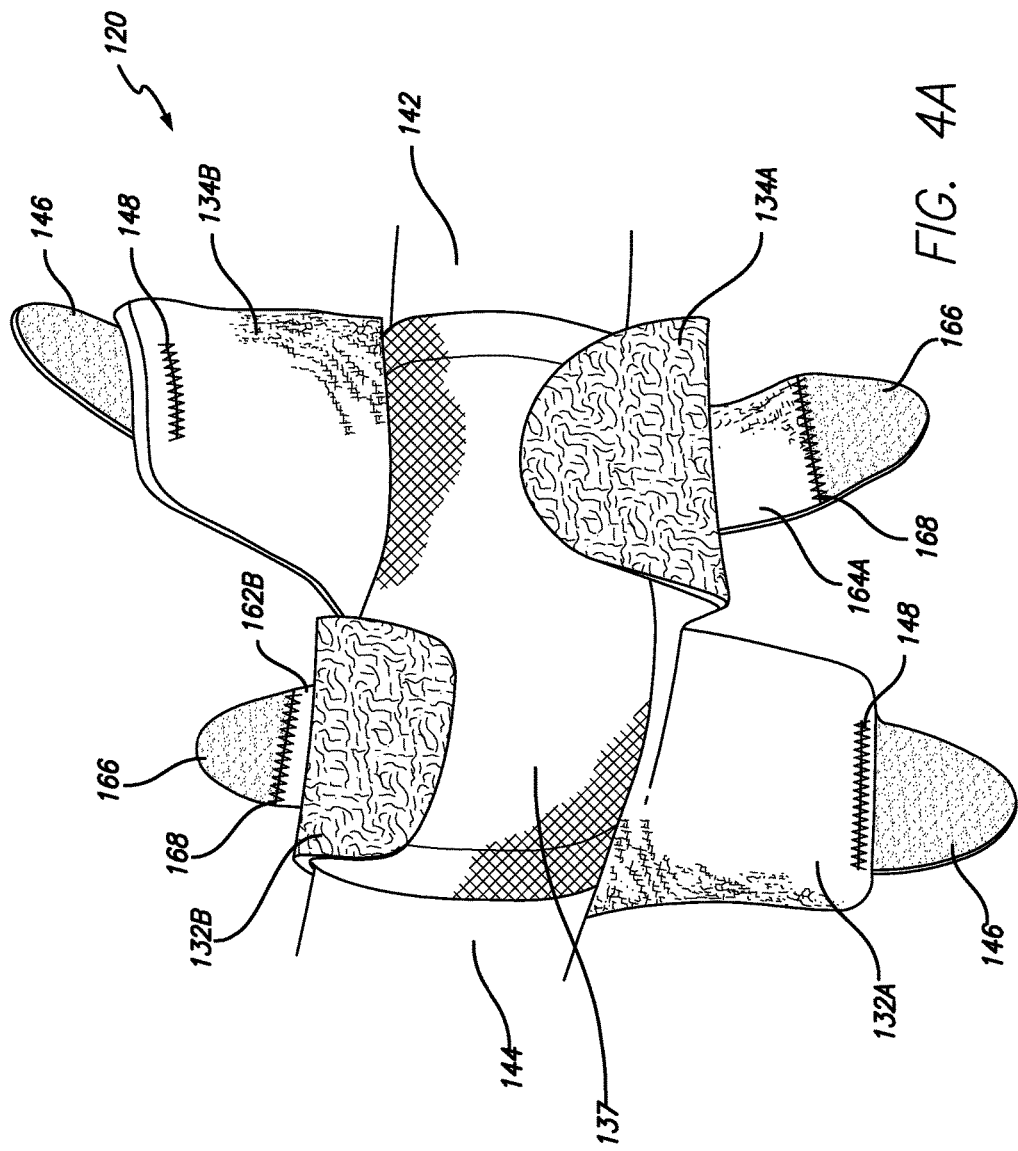

ELBOW BRACE

CROSS REFERENCE TO RELATED APPLICATIONS

This application claims priority to provisional application No. 61/829,248 filed May 31, 2013, the disclosure of which is incorporated by reference.

FIELD OF THE INVENTION

This invention relates generally to the field of articles worn by persons to reduce the likelihood, severity, or exacerbation of injury to the body, and more specifically to the field of braces worn on the elbow.

BACKGROUND OF THE INVENTION

Flexible elbow braces are used by athletes and other persons engaged in vigorous physical activity to protect the elbow from injury and to avoid exacerbation of existing injury. The elbow is one of the most heavily used joints of the body, as it is used in any activity that involves the use of the hands, such as throwing, striking, carrying, or swinging a tennis racquet or baseball bat. The elbow is also a common subject of injury, due to the relatively high levels of stress it must bear. During normal daily activities, in occupations involving physical labor, and especially during strenuous sports, the elbow can undergo abnormal motions as a result of quick changes in direction, falls, fatigue, uneven surfaces, or impacts. These abnormal motions can cause sprains or more serious injuries, including dislocation, stretching, or tearing of the tissues that make up the elbow.

Devices to protect the elbow against abnormal motions have been used for many years, in a variety of specific embodiments which vary in their abilities to protect against the different types of abnormal motions. One such elbow brace is shown in FIGS. 6-8 of U.S. Pat. No. 5,472,413. However, the protections afforded by these devices against abnormal motion are often accompanied by a reduction in range or ease of normal motion, and may be accompanied by other undesirable aspects such as poor performance, added weight, difficulty of application, fit, cost, and/or appearance.

For these reasons, there has long been motivation to find an improved elbow brace which can protect and support the elbow without affecting the range or ease of normal motion, while avoiding the undesirable aspects of prior art devices.

SUMMARY OF THE INVENTION

In a preferred embodiment, a elbow brace according to the present invention includes a base and a tension member having pairs of upper-arm and forearm tensioning straps, wherein the tension member is permanently fastened to the interior surface of the base, between the base and the arm of the person when worn.

According to another aspect of the invention, a elbow brace according to the present invention includes a base and a tension member having pairs of upper-arm and forearm tensioning straps, wherein the tension member is permanently fastened to the base by a plurality of stitches through the mid-line axes of the base and tension member.

According to another aspect of the invention, a elbow brace according to the present invention includes a base with pairs of upper-arm and forearm apertures, and a tension member positioned between the base and the arm of the person when worn and having pairs of upper-arm and forearm tensioning straps, wherein the tensioning straps extend through the apertures in the base when the brace is worn.

Further objects, features, and advantages of the invention will be apparent from the following detailed description when taken in conjunction with the accompanying drawings.

BRIEF DESCRIPTION OF THE DRAWINGS

In the drawings:

FIG. 4A is a top view of the elbow brace of FIGS. 3A-3C, applied to the arm of a person with both the base mounting straps and the tension straps unfastened;

DETAILED DESCRIPTION OF THE INVENTION

Figure 1A:
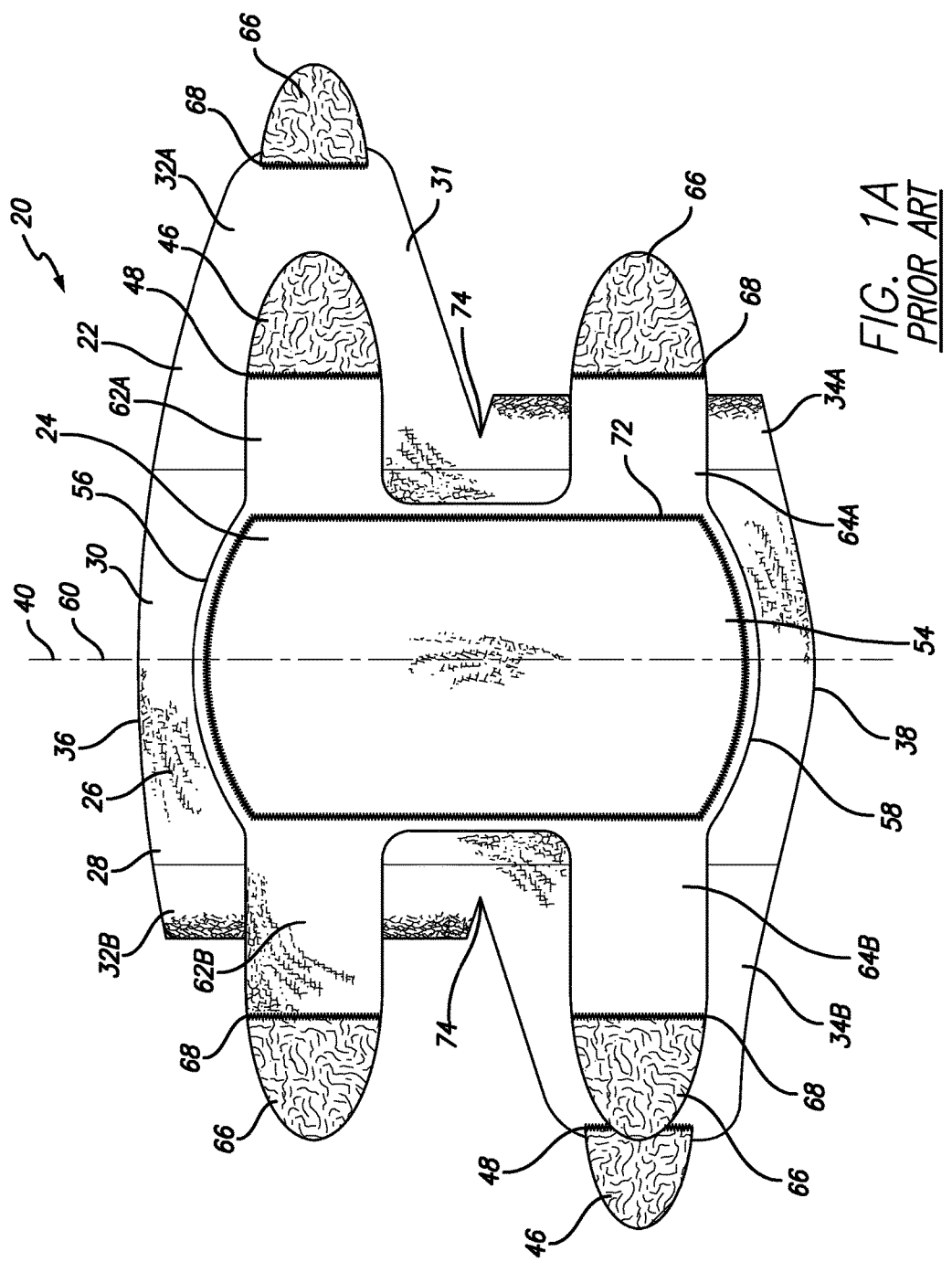
FIG. 1A is a plan view of a prior art elbow brace, laid flat to expose the exterior surface of the brace.
Figure 1B:
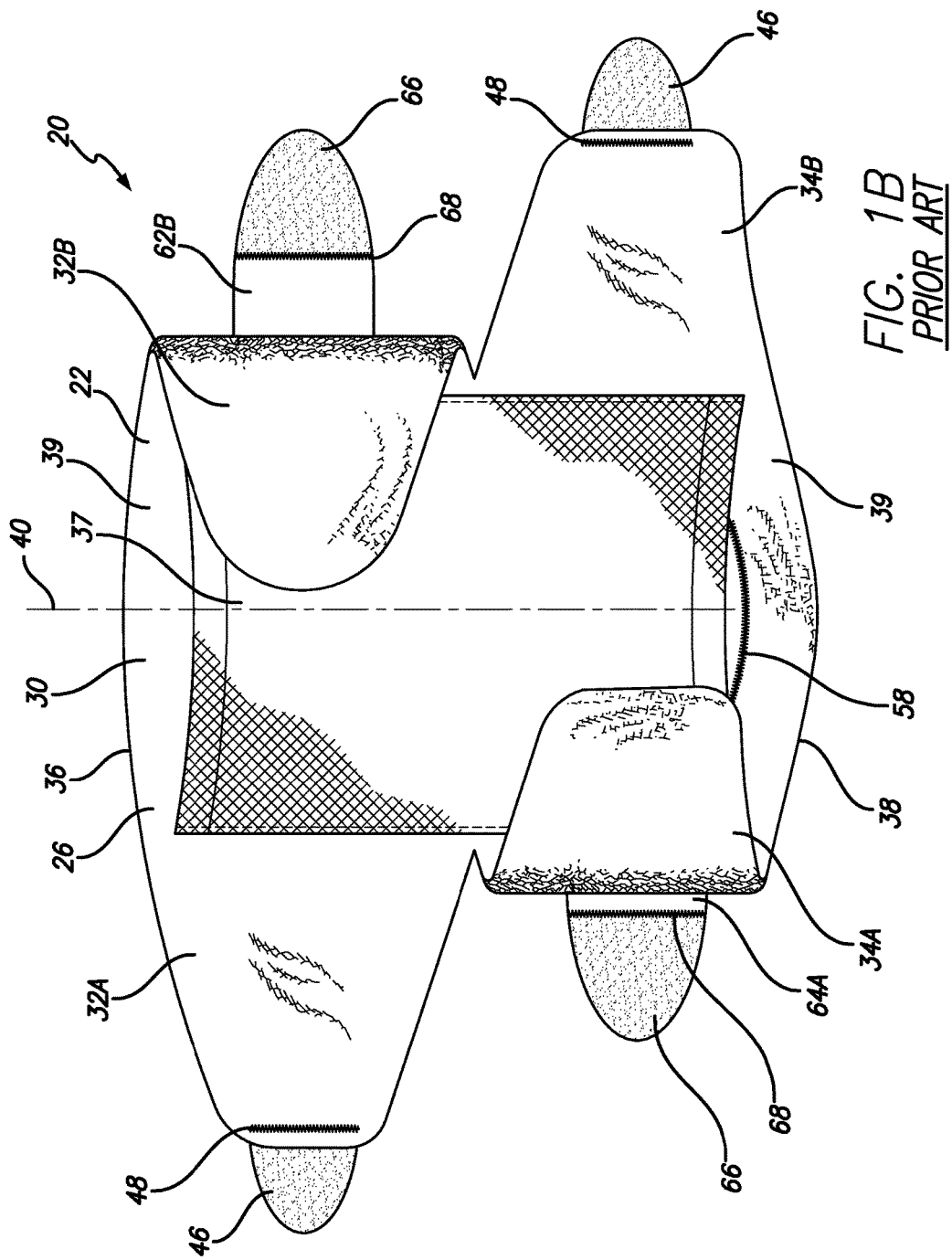
FIG. 1B is a plan view of the prior art elbow brace of FIG. 1A, laid flat to expose the interior surface of the brace.

Referring to the drawings, FIGS. 1A and 1B show a prior art elbow brace 20, similar to the design taught in U.S. Pat. No. 5,472,413, the contents of which are hereby incorporated by reference. The prior art elbow brace 20 includes a base member 22 and a spider member 24, each made by cutting planar sheets 26 of an elastomeric material into the desired shapes. The exterior surface 31 of the base member 22 is covered with fabric bearing fiber loops 28 that adheres to hook-type material when the fiber loops and hook-type material are pressed together.

The base 22 of the prior art elbow brace 20 has a base central portion 30 extending vertically from an upper edge 36 to a lower edge 38, and has a mid-line axis 40 running vertically down the middle of base central portion 30. The base 22 includes a first upper mounting strap 32A, a second upper mounting strap 32B, a first lower mounting strap 34A, and a second lower mounting strap 34B extending from the central portion 30.

As perhaps best shown in FIG. 1B which shows the interior surface 39 of the base 22, the first upper mounting strap 32A and first lower mounting strap 34B terminate in hook-type strap fastening tabs 46 suitable for detachable attachment to the fabric bearing fiber loops 28 on the exterior surface 31 of the base member 22. The strap fastening tabs 46 are sewn to the mounting straps with stitches 48. An application sleeve 37 is sewn to the sides of the interior surface 39 of the base, for ease of application.

The base may be formed to include a recess 74 to prevent bunching when the brace is worn, and the base may include edge binding, although these features are not required.

As perhaps best shown in FIG. 1A which shows the exterior surface 31 of the base 22, the prior art elbow brace 20 includes a spider member 24. The spider member 24 has a spider member central portion 54 extending vertically from an upper edge 56 to a lower edge 58, and has a mid-line axis 60 running vertically down the middle of the tension member central portion 54. The spider member 24 is permanently attached to the exterior surface 31 of the base 22 by stitches 72 that extend around the periphery of the spider member central portion 54.

The spider member 24 includes a first upper tensioning strap 62A, a second upper tensioning strap 62B, a first lower tensioning strap 64A, and a second lower tensioning strap 64B extending from the central portion 54. Each of the tensioning straps 62A, 62B, 64A, 64B terminates in hook-type fastening tabs 66, suitable for detachable attachment to the loop-type fabric 28 on the exterior surface of the base 22 and sewn to the tensioning straps with stitches 68.

Figure 2A:
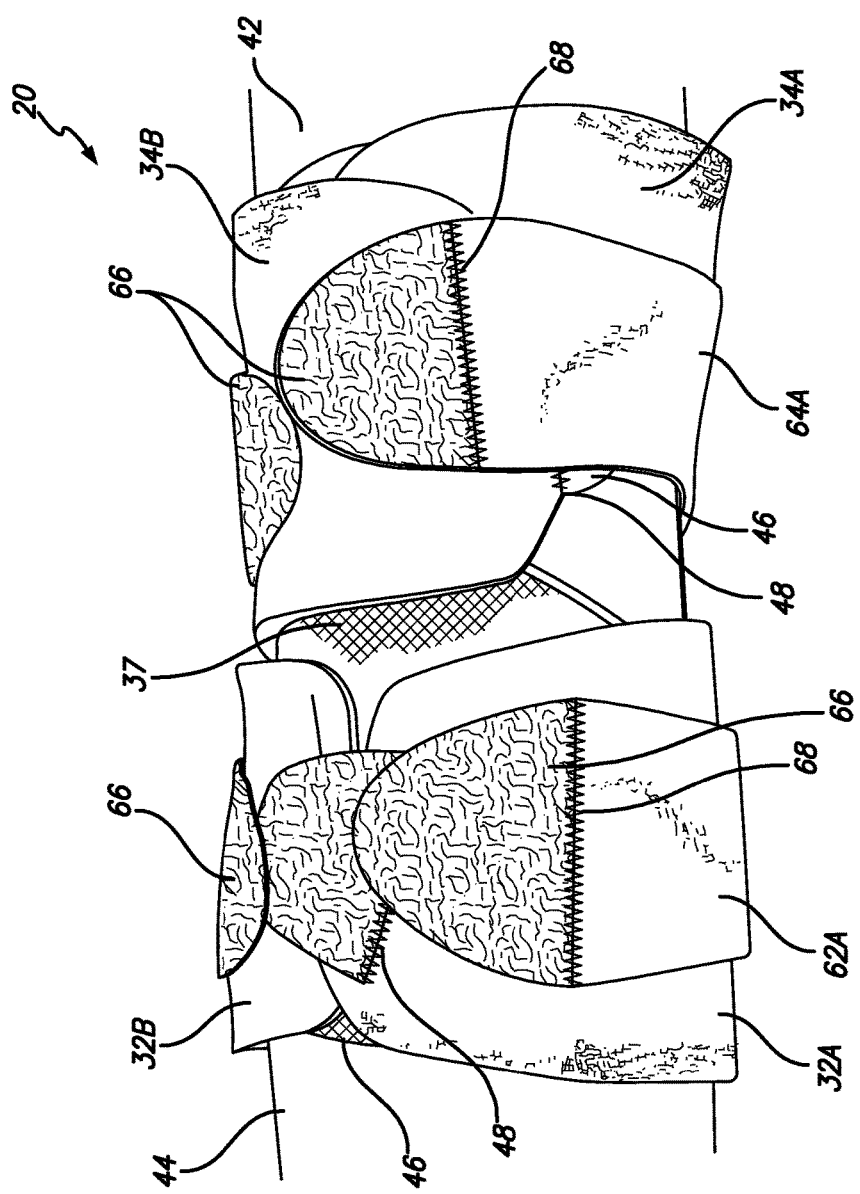
FIG. 2A is a top view of the elbow brace of FIGS. 1A-1B, applied to the arm of a person with both the base mounting straps and tension straps fastened.
Figure 2B:
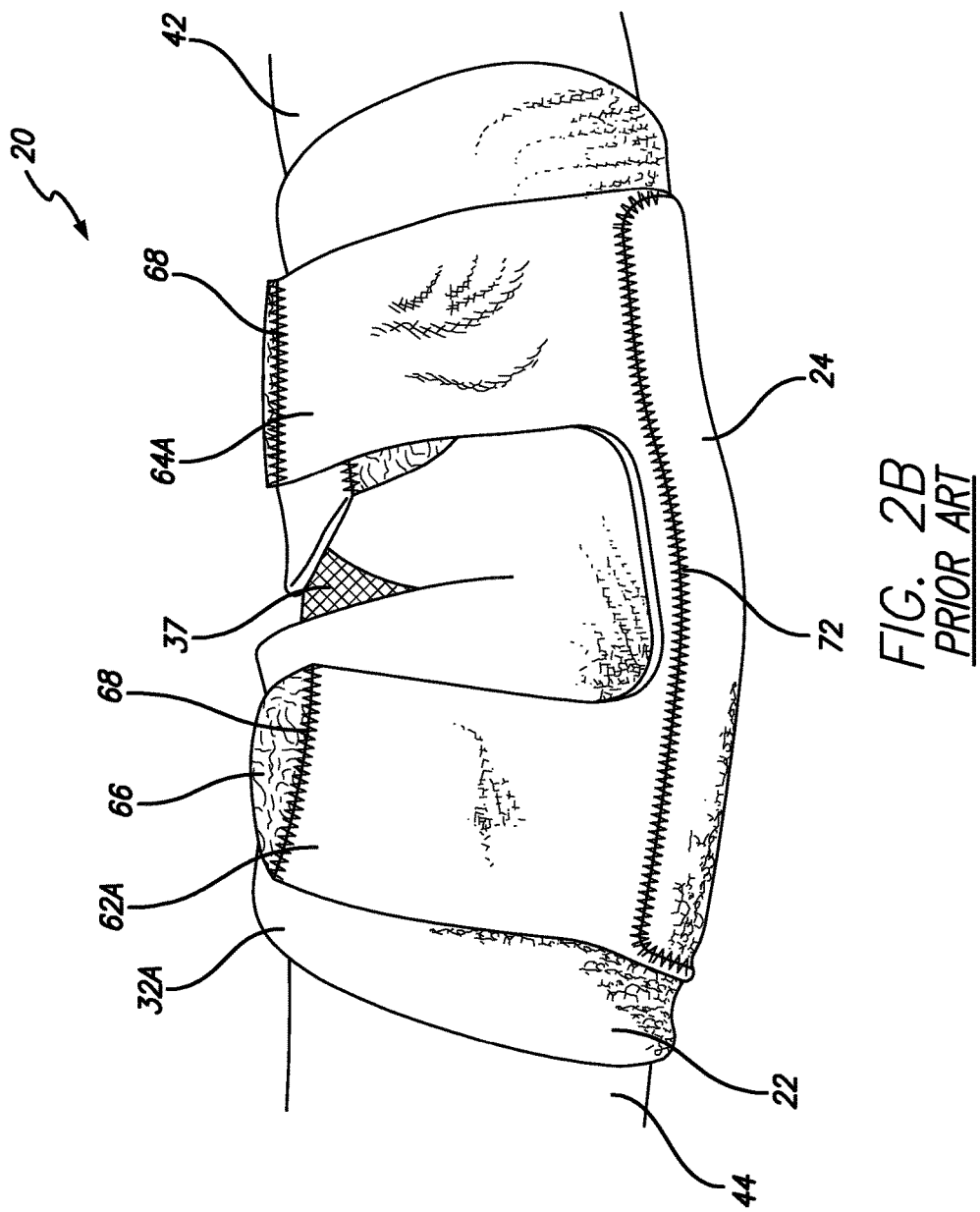
FIG. 2B is a side view of the elbow brace of FIGS. 1A-1B, applied to the arm of a person with both the base mounting straps and tension straps fastened.

FIGS. 2A and 2B are top and side views, respectively, of the elbow brace 20 of FIGS. 1A-1B, applied to the arm of a person with both the base mounting straps and tension straps fastened. When worn, the brace 20 is first applied to the elbow and surrounding portions of the upper-arm 44 and forearm 42 of the wearer by the application sleeve 37. The first upper-arm mounting strap 32A is stretched to overlap the second upper-arm mounting strap 32B on the upper-arm 44 above the elbow, allowing the hook-type fastening tab 46 at the end of the first upper mounting strap 32A to adhere to the fabric bearing fiber loops 28 on the exterior surface of the second upper mounting strap 32B in order to fasten the elbow brace 20 about the upper arm 44 of the wearer. Similarly, the first forearm mounting strap 34A overlaps and adheres to the second forearm mounting strap 34B on the forearm 42 in order to fasten the elbow brace 20 about the forearm 42 of the wearer.

Figure 3A:
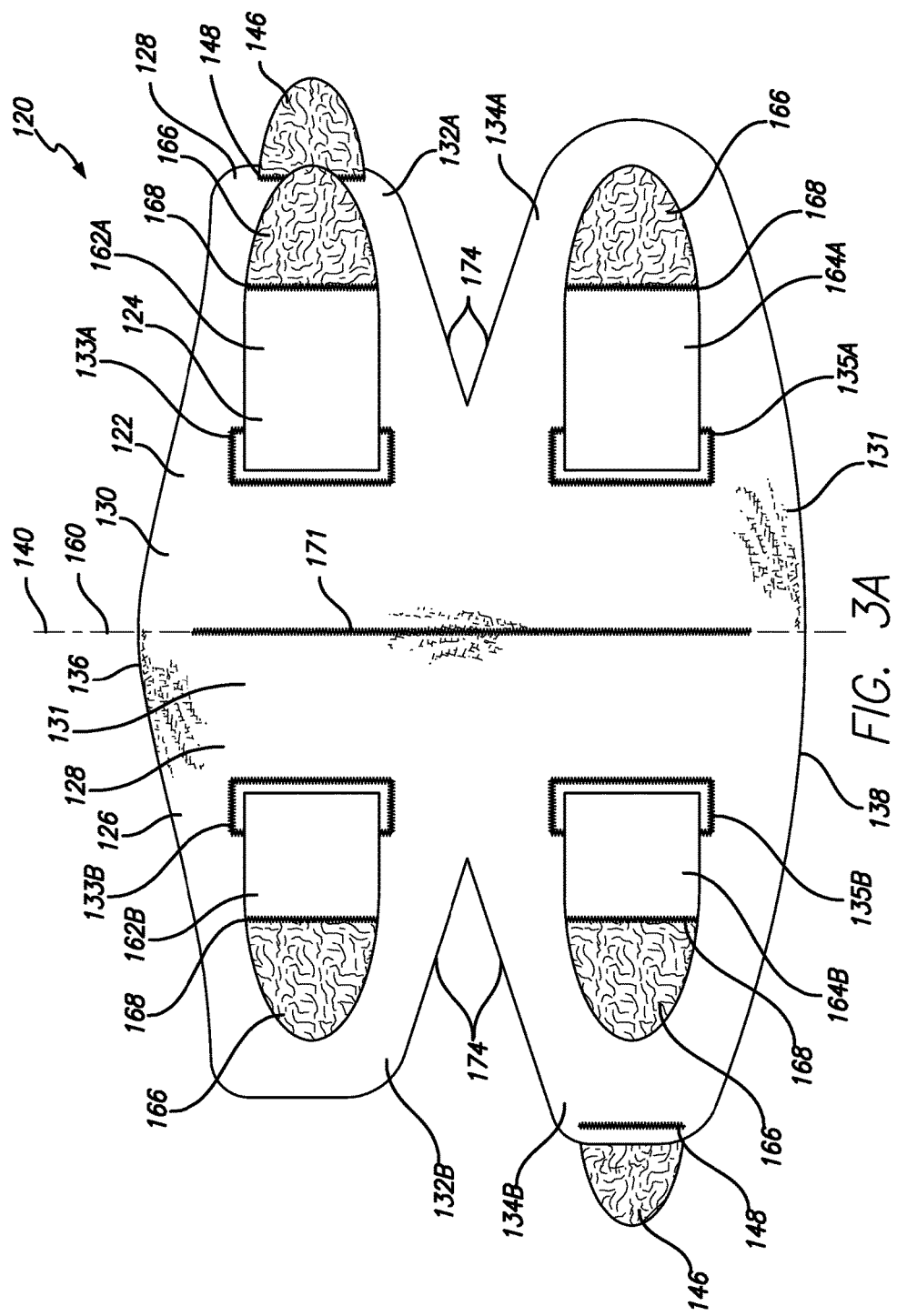
FIG. 3A is a plan view of a elbow brace according to the present invention, laid flat to expose the exterior surface of the brace.
Figure 3B:
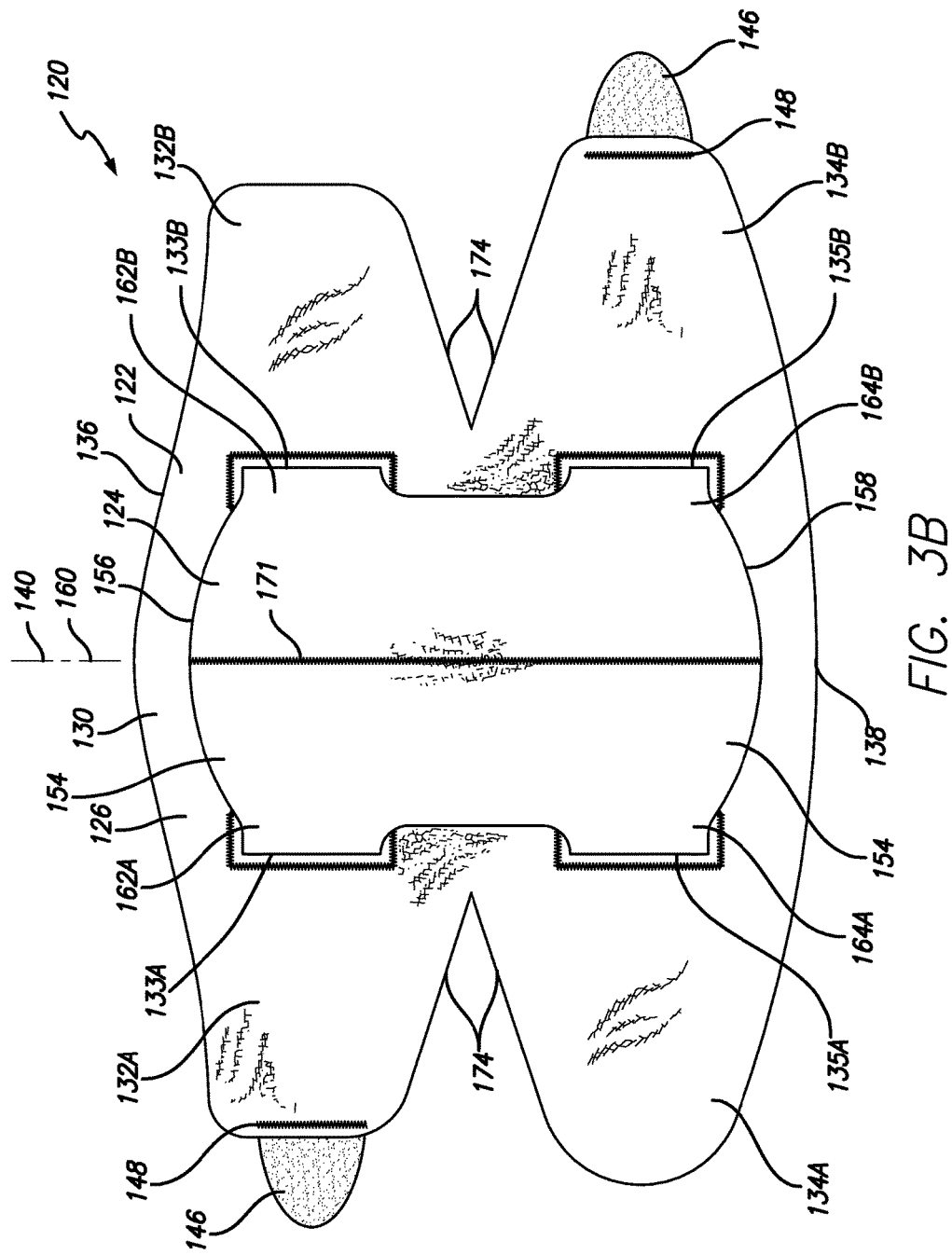
FIG. 3B is a plan view of the elbow brace of FIG. 3A, with the brace laid flat and with the application sleeve removed to expose the tension member on the interior surface of the brace.
Figure 3C:
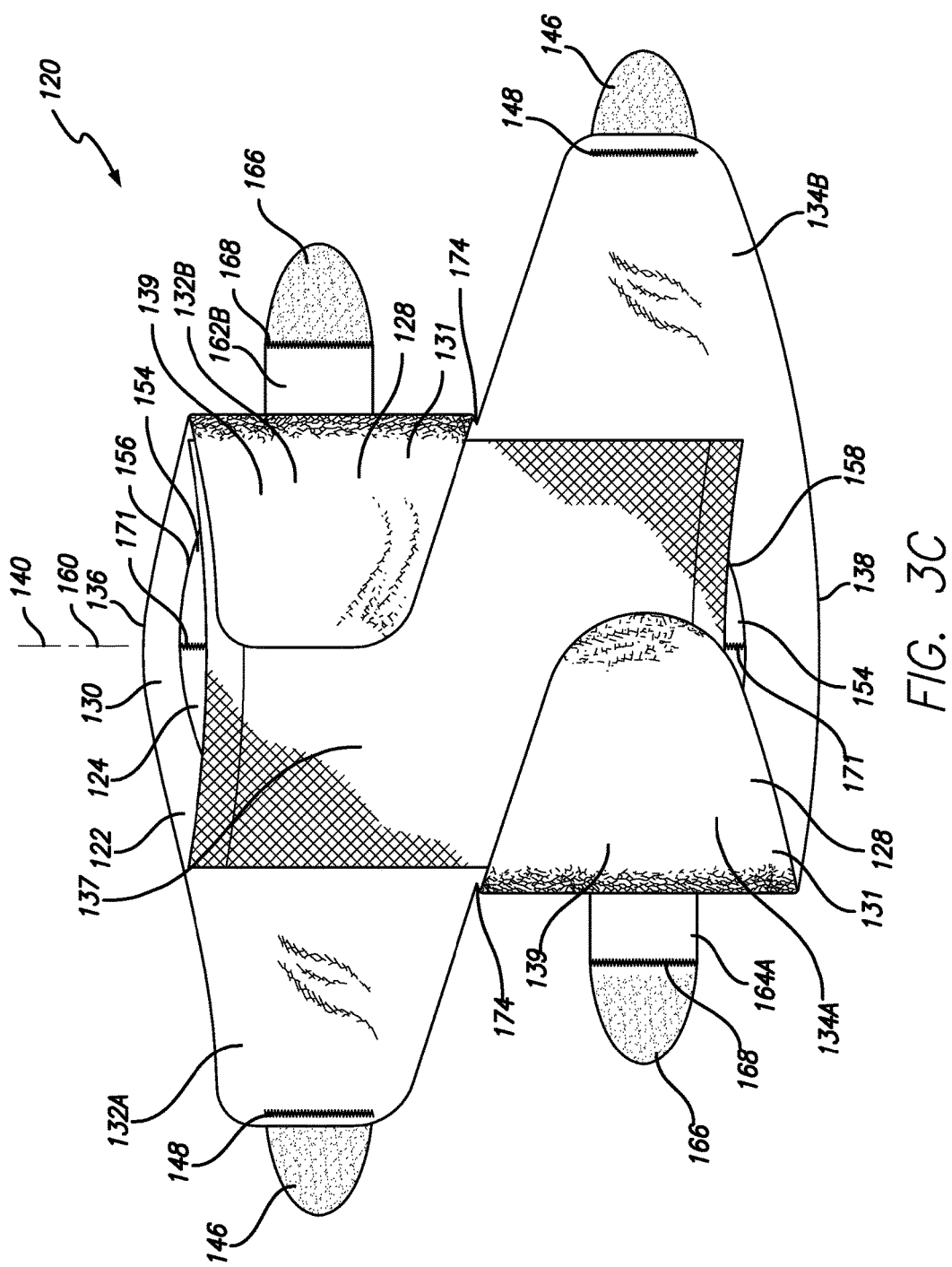
FIG. 3C is a plan view of the elbow brace of FIG. 3A, with the application sleeve in place.

FIG. 3A shows the exterior of an elbow brace 120 according to the present invention laid flat. FIGS. 3B and 3C show the interior of the elbow brace 120, with the application sleeve 137 removed in FIG. 3B to show the internal construction of the brace 120. The elbow brace 120 includes a base 122 and a tension member 124 mounted on the inside of the base 122, each made by cutting planar sheets 126 of an elastomeric material into the desired shapes. The outer surface of the base 122 is preferably covered with fabric bearing fiber loops 128 that adheres to hook-type material when the fiber loops and hook-type material are pressed together.

The base 122 of the elbow brace 120 has a base central portion 130 extending vertically from a lower edge 136 to an upper edge 138, and has a mid-line axis 140 running vertically down the middle of the base central portion 130. The base 122 includes a first upper-arm mounting strap 134A, a second upper-arm mounting strap 134B, a first forearm mounting strap 132A, and a second forearm mounting strap 132B extending from the central portion 130. The first and second upper-arm mounting straps 134A, 134B may be formed somewhat larger that the first and second forearm mounting straps 132A, 132B, to better fit the limb portions to which each is applied.

The base 122 may be formed to include a recess 174 between the upper-arm mounting straps 134A, 134B and the forearm mounting straps 132A, 132B, so that when the elbow brace 120 is fitted upon the elbow a gap exists to provide ventilation and help avoid bunching or undue restriction of movement.

The base 122 is preferably formed, as shown in FIGS. 3A-3B, as a reclosable sleeve made from a sheet of elastic material that provides generalized support and compression to the elbow area, along with therapeutic warming, but other materials may be used. The base 122 may also be formed, for example, as a tubular elastic sleeve shaped to fit snugly about the elbow. The base may include edge binding, although this is not required.

As perhaps best shown in FIG. 3B which shows the interior surface 139 of the base 122 with the application sleeve 137 removed, the first upper-arm mounting strap 134B and first forearm mounting strap 132A terminate in hook-type strap fastening tabs 146 suitable for detachable attachment to the fabric bearing fiber loops 128 on the external surface 131 of the base 122. The hook-type strap fastening tabs 146 are sewn to the mounting straps with stitches 148. As shown in FIG. 3C, the complete brace 120 includes an application sleeve 137 sewn to the sides of the interior surface 139 of the base, for ease of application.

As perhaps best shown in FIG. 3B which shows the interior surface 139 of the base 122, the elbow brace 120 includes a tension member 124. The tension member 124 has a tension member central portion 154 extending vertically from an upper edge 158 to a lower edge 156, and has a mid-line axis 160 running vertically down the middle of the tension member central portion 154. The central portion 154 of the tension member 124 is permanently attached to the interior surface 139 of the base 122 by stitches 171 that extend along the mid-line axis 160 of the tension member central portion 54.

The tension member 124 includes a first upper-arm tensioning strap 164A, a second upper-arm tensioning strap 164B, a first forearm tensioning strap 162A, and a second forearm tensioning strap 162B extending from the central portion 154. Each of the tensioning straps 162A, 162B, 164A, 164B terminates in hook-type fastening tabs 166 suitable for detachable attachment to the fabric bearing fiber loops 128 on the exterior surface of the base 122 and sewn to the tensioning straps with stitches 168.

Figure 4B:
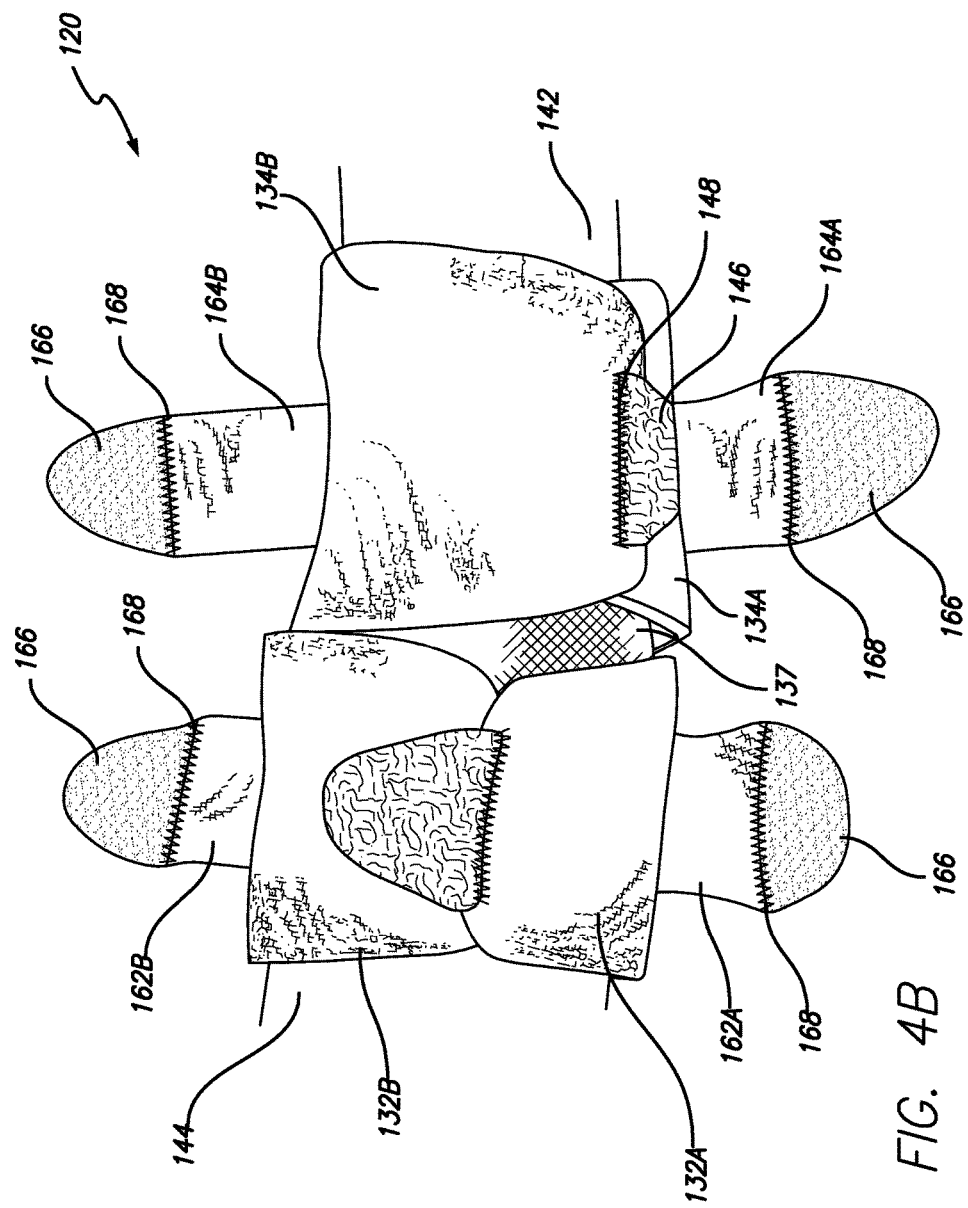
FIG. 4B is a top view of the elbow brace of FIGS. 3A-3C, applied to the arm of a person with the base mounting straps fastened and the tension straps unfastened.
Figure 4C:
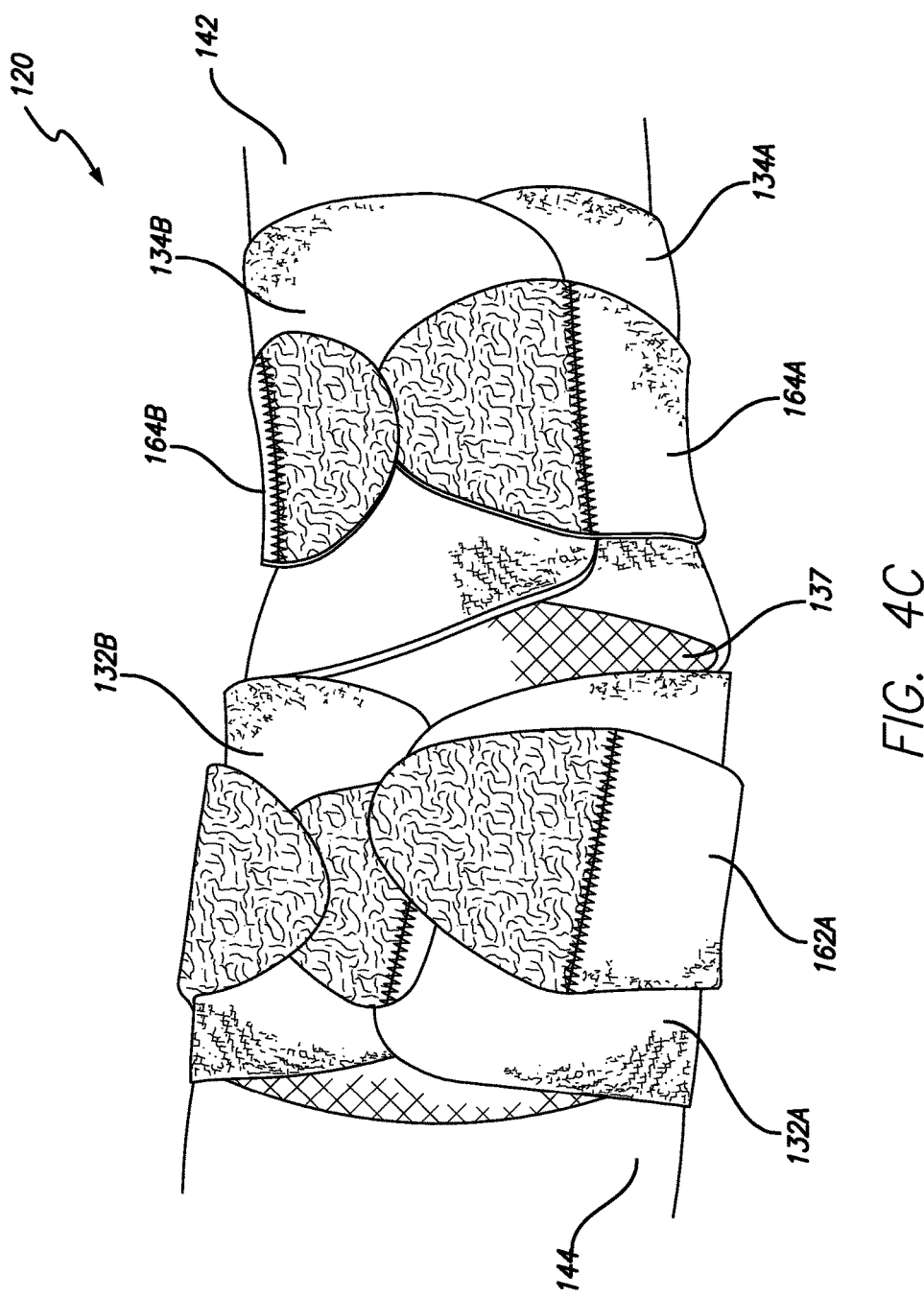
FIG. 4C is a top view of the elbow brace of FIGS. 3A-3C, applied to the arm of a person with both the base mounting straps and the tension straps fastened.
Figure 4D:
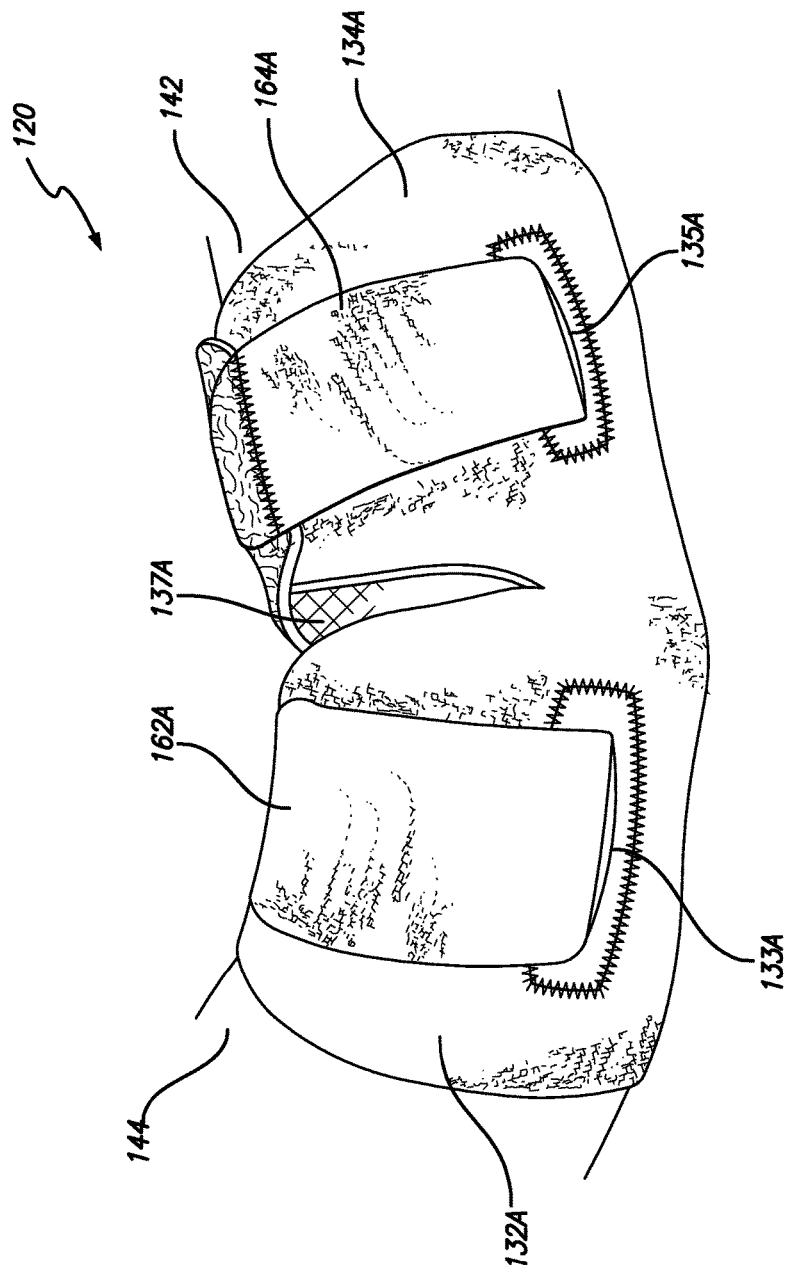
FIG. 4D is a side view of the elbow brace of FIGS. 3A-3C, applied to the arm of a person with both the base mounting straps and the tension straps fastened.
Figure 4E:
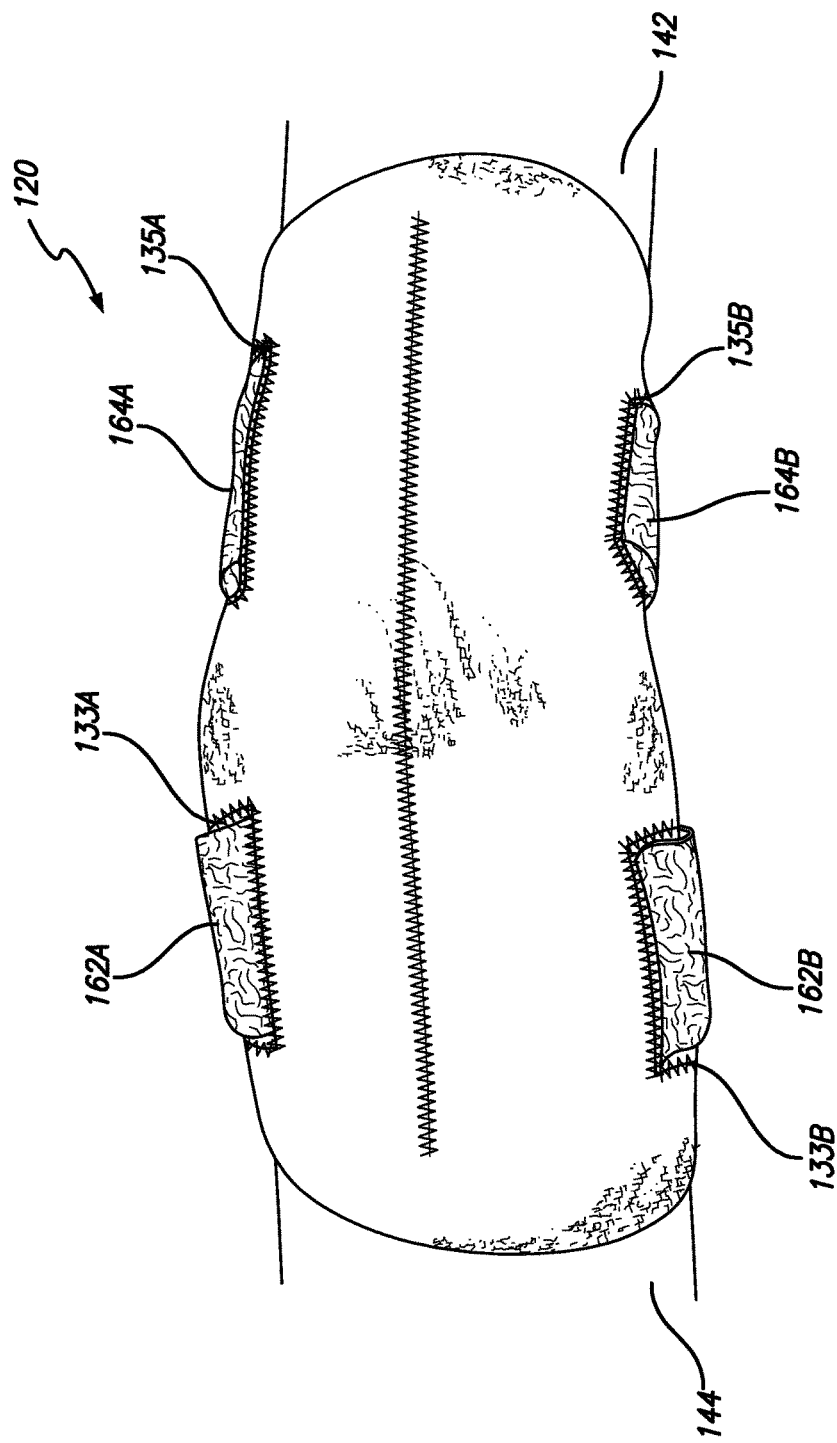
FIG. 4E is a bottom view of the elbow brace of FIGS. 3A-3C, applied to the arm of a person with both the base mounting straps and the tension straps fastened.

FIGS. 4A and 4B are top views of the elbow brace 120 on the arm of a person, with the mounting straps unfastened in FIG. 4A and fastened in FIG. 4B. When worn, the brace 120 is first applied to the elbow and surrounding portions of the upper-arm 142 and forearm 144 of the wearer by the application sleeve 137, as shown in FIG. 4A.

FIG. 4B shows the first upper-arm mounting strap 134A stretched to overlap the second upper-arm mounting strap 134B on the upper-arm 142 above the elbow, allowing the hook-type fastening tab 146 at the end of the first upper-arm mounting strap 134A to adhere to the fabric bearing fiber loops 28 on the exterior surface of the second upper-arm mounting strap 134B in order to fasten the elbow brace 120 about the upper arm 142 of the wearer. Similarly, the first forearm mounting strap 132A is stretched to overlap and adhere to the second forearm mounting strap 132B on the forearm 144 in order to fasten the elbow brace 120 about the forearm 144 of the wearer.

FIG. 4B shows the first upper-arm mounting strap 134A stretched to overlap the second upper-arm mounting strap 134B on the upper-arm 142 above the elbow, allowing the hook-type fastening tab 146 at the end of the first upper-arm mounting strap 134A to adhere to the fabric bearing fiber loops 28 on the exterior surface of the second upper-arm mounting strap 134B in order to fasten the elbow brace 120 about the upper arm 142 of the wearer. Similarly, the first forearm mounting strap 132A is stretched to overlap and adhere to the second forearm mounting strap 132B on the forearm 144 in order to fasten the elbow brace 120 about the forearm 144 of the wearer.

FIGS. 4C, 4D, and 4E top, side, and bottom views, respectively, of the elbow brace 120 applied to the arm of a person, as in FIG. 4B but additionally with both pairs of tension straps fastened. The first upper-arm tensioning strap 164A and the second upper-arm tensioning strap 164B are each stretched to a desired level of tension, then the hook-type fastening tabs 166 at the ends of the straps 164A, 164B are pressed to adhere to the fabric bearing fiber loops 28 on the exterior surface 131 of the base 122 or the exterior surface of the mounting strap fastening tabs 146. Similarly, the first and second forearm tensioning straps 162A, 162B are each stretched to a desired level of tension, then the hook-type fastening tabs 166 at the ends of the straps 164A, 164B are pressed into place on the base 122.

While there are some similarities between the prior art elbow brace 20 and a elbow brace 120 according to the present invention, there are (without limitation) at least three important differences. First, the spider member 24 of the prior art elbow brace 20 is fastened to the exterior surface 31 of the base 22. In contrast, the tension member 124 of the elbow brace 120 according to the present invention is fastened to the interior surface 139 of the base 122.

Second, the spider member 24 of the prior art elbow brace 20 is fastened to the base 22 by stitches 72 that extend around the periphery of the tension member central portion 54. In contrast, the tension member 124 of the elbow brace 120 is fastened to the base 122 by a single line of stitches 171 extending along the mid-line axis 160 of the tension member central portion 154.

Third, both the central portion 54 and the tensioning straps 62A, 62B, 64A, 64B of the tension member 24 of the prior art elbow brace 20 are on the exterior surface 31 of the base 22 during normal use. In contrast, in the elbow brace 120 the central portion 154 of the tension member 124 is on the interior surface 139 of the base 122, and (as perhaps best shown in FIG. 4E) the tensioning straps 162A, 162B, 164A, and 164B extend through apertures 133A, 133B, 135A, 135B to reach the exterior surface 131 of the base 122.

Figure 5A:
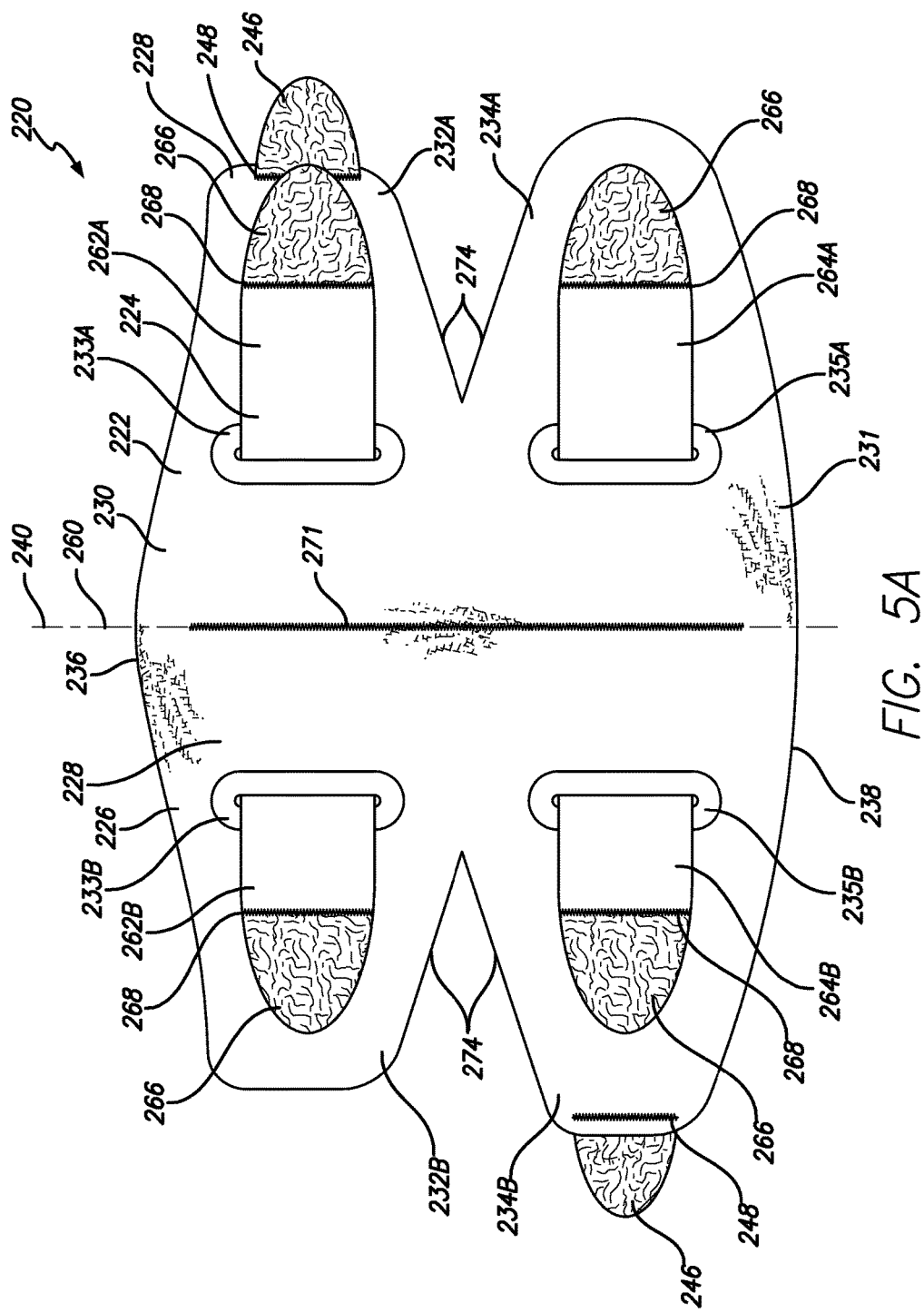
FIG. 5A is a plan view of a second embodiment of an elbow brace according to the present invention, laid flat to expose the exterior surface of the brace.

FIG. 5A shows the exterior of a second embodiment of an elbow brace 220 according to the present invention laid flat. The elbow brace 220 is similar to the elbow brace 120, and is applied to the elbow in a similar fashion. However, the elbow brace 220 includes a different tension member 224 comprising tension member strap portions 262A, 262B, 264A, 264B and an anchor portion 225 permanently fastened to the base member 222, for example by stitching. The elbow brace 220 also includes reinforced apertures (eyelets) 233A, 233B, 235A, 235B.

Figure 5B:
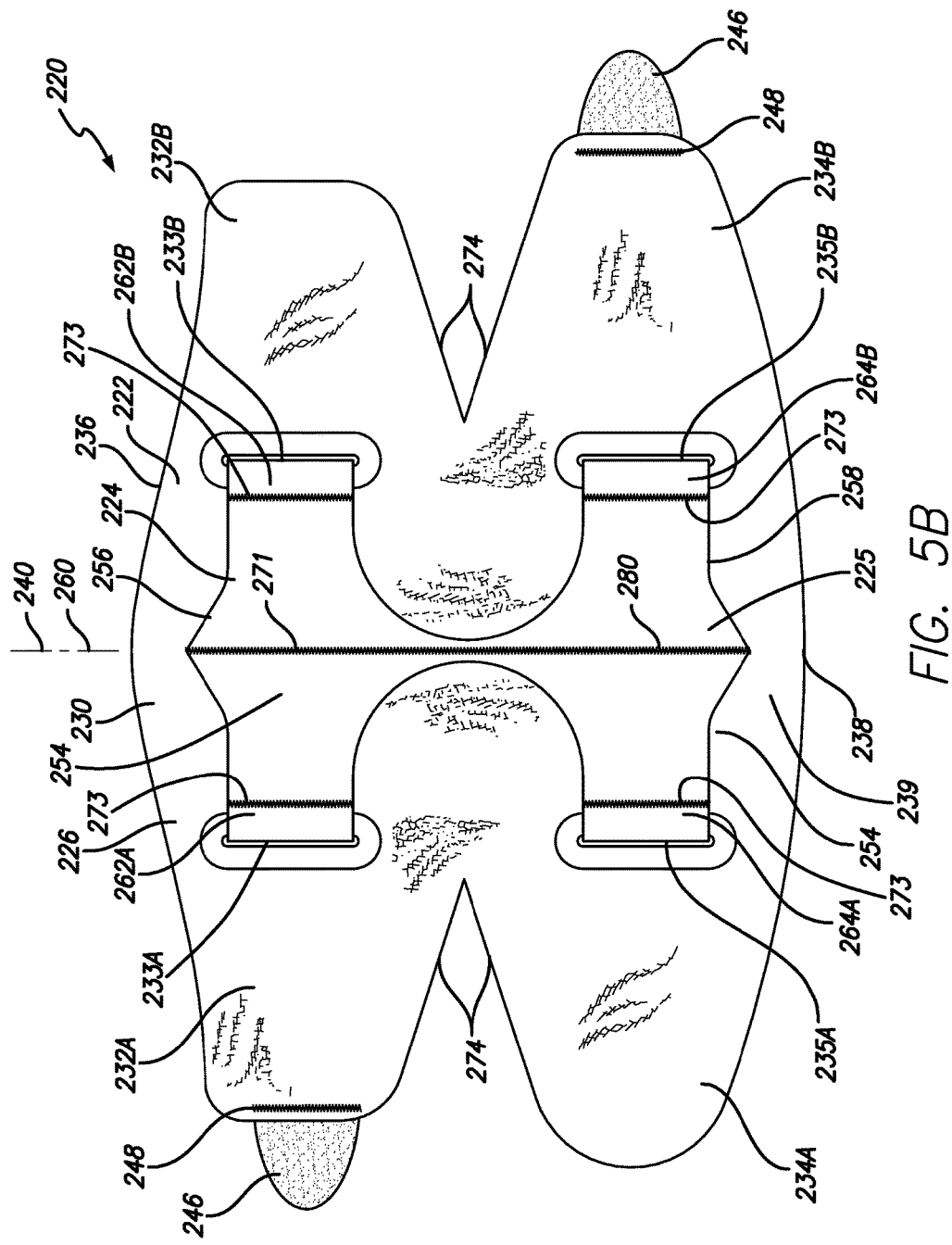
FIG. 5B is a plan view of the elbow brace of FIG. 5A, laid flat and with the application sleeve removed to expose the interior surface of the brace.

FIG. 5B shows the interior construction of the elbow brace 220, with the application sleeve that would normally be present (like application sleeve 137 in elbow brace 120) removed to show the internal construction of the brace 220. Like the brace 120, the elbow brace 220 includes a base 222 with the tension member 224 mounted on the inside of the base 222. The base 222 is made by cutting one or more planar sheets 226 of an elastomeric material into the desired shape. The outer surface of the base 222 is preferably covered with fabric bearing fiber loops 228 that adheres to hook-type material when the fiber loops and hook-type material are pressed together.

The base 222 of the elbow brace 220 has a base central portion 230 extending vertically from a lower edge 236 to an upper edge 238, and has a mid-line axis 240 running vertically down the middle of the base central portion 230. The base 222 includes a first upper-arm mounting strap 234A, a second upper-arm mounting strap 234B, a first forearm mounting strap 232A, and a second forearm mounting strap 232B extending from the central portion 230. The first and second upper-arm mounting straps 234A, 234B may be formed somewhat larger that the first and second forearm mounting straps 232A, 232B, to better fit the limb portions to which each is applied.

The base 222 may be formed to include a recess 274 between the upper-arm mounting straps 234A, 234B and the forearm mounting straps 232A, 232B, so that when the elbow brace 220 is fitted upon the elbow a gap exists to provide ventilation and help avoid bunching or undue restriction of movement.

The base 222 is preferably formed, as shown in FIGS. 5A-5B, as a reclosable sleeve made from a sheet of elastic material that provides generalized support and compression to the elbow area, along with therapeutic warming, but other materials may be used. The base 222 may also be formed, for example, as a tubular elastic sleeve shaped to fit snugly about the elbow. The base may include edge binding, although this is not required.

The first upper-arm mounting strap 234B and first forearm mounting strap 232A terminate in hook-type strap fastening tabs 246 suitable for detachable attachment to the fabric bearing fiber loops 228 on the external surface 231 of the base 222. The hook-type strap fastening tabs 246 are sewn to the mounting straps with stitches 248. Although not shown in FIG. 5B, the complete brace 220 preferably includes an application sleeve sewn to the sides of the interior surface 239 of the base for ease of application, like the application sleeve 137 in brace 120.

The elbow brace 220 includes a tension member 224 extending vertically from an upper edge 258 to a lower edge 256, with a tension member central portion 254 and a tension member mid-line axis 260. The tension member 224 comprises an anchor portion 225 permanently fastened to the base 222 and strap portions 262A, 262B, 264A, 264B that extend through the apertures 233A, 233B, 235A, 235B. The anchor portion 225 is preferably formed of a synthetic fiber that is relatively elastic in all directions, for example of the type known as spandex in the United States or elasthane, or sold under the trademark LYCRA®, although this is not required and other materials could be used.

Figure 6:
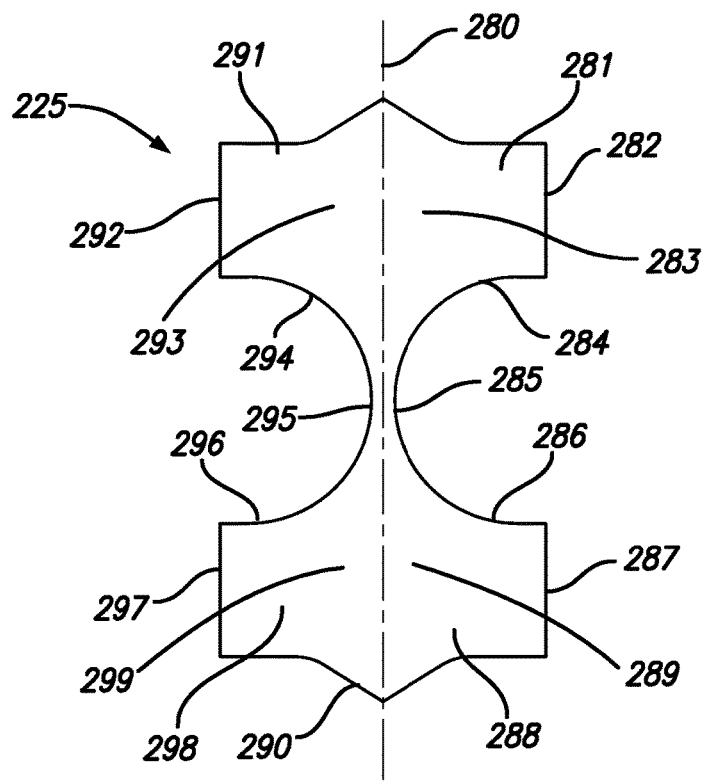
FIG. 6 is a plan view of the anchor portion of the tension member of the elbow brace of FIGS. 5A-5B.

As perhaps best shown in FIG. 6, the anchor portion 225 has an anchor portion centerline 280. The anchor portion 225 has upper arms 288, 298 extending laterally from the centerline 280 through middle portions 289, 299 to upper arm ends 287, 297, and lower arms 281, 291 extending laterally from the centerline 280 through middle portions 283, 293 to lower arm ends 282, 292. As shown in FIG. 5B, upper arm ends 287, 297 are attached to strap portions 264A, 264B by stitches 273, and lower arm ends 282, 292 are attached to strap portions 262A, 262B by stitches 273.

The upper and lower portions of the anchor portion 225 may include points 290. The central portions 285, 295 of the anchor portion 225 may be narrower than the length of the upper arms 288, 298 and the lower arms 281, 291, as shown in FIGS. 5B and 6. The anchor portion 225 includes a roughly semi-circular shape along the points 284-285-286 and along points 294-295-295. However this is not the only shape that could be used, for example an oval, rectangle, parabola, hyperbola, or triangle shape, symmetric or asymmetric, could be used between the upper arms 288, 298 and the lower arms 281, 291.

As perhaps best shown in FIG. 5B, the tension member anchor portion 225 is permanently fastened to the interior surface 239 of the base 222 with stitches, preferably with a single line of center stitches 271 along the tension member anchor portion centerline 280 and tension member centerline 260. However, this is not required and the anchor portion 225 can be permanently fastened to the base 222 at a fewer or a greater number of locations, or at different locations.

The strap portions 262A, 262B, 264A, 264B can be formed of an elastomeric material that is somewhat less elastic compared to the anchor portion 225, and could be, for example, the same coated polyurethane foam material bearing fabric loops 228 used for the base 222. The material for the strap portions 262A, 262B, 264A, 264B is preferably elastic along the length of the straps, but with little elasticity across the width of the straps, instead of being elastic in all directions like the anchor portion 225.

The tension member strap portions 262A, 262B, 264A, 264B extend through apertures 233A, 233B, 235A, 235B and terminate in hook-type fastening tabs 266 sewn to the tensioning straps with stitches 268 and suitable for detachable attachment to the fabric bearing fiber loops 128 on the exterior surface of the base 122.

Figures 7A, 7B:
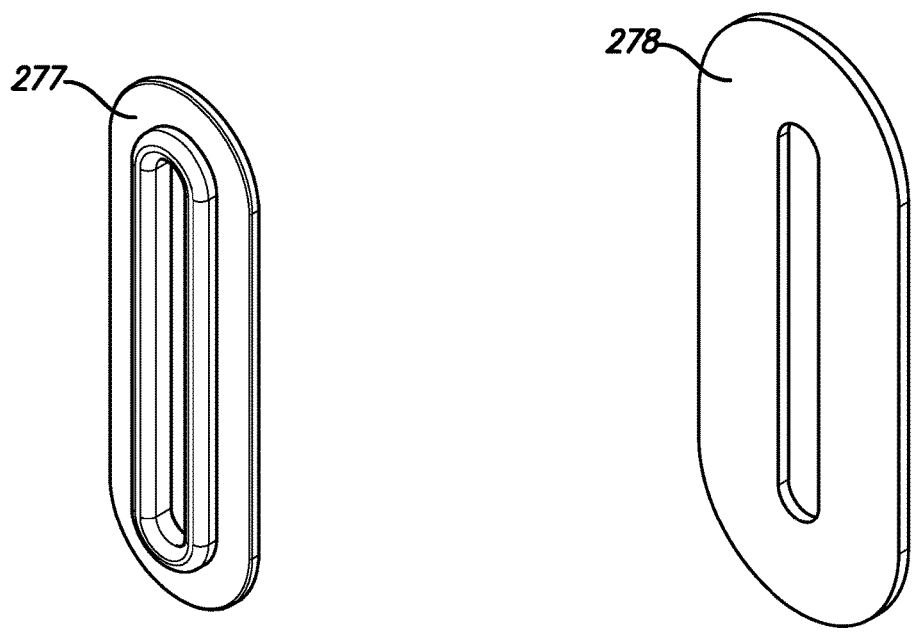
FIG. 7A is a perspective view of an aperture reinforcement base for use in the elbow brace of FIGS. 5A-5B.
FIG. 7B is a perspective view of an aperture reinforcement backing for use in the elbow brace of FIGS. 5A-5B.

FIGS. 7A and 7B show an aperture reinforcement base 277 and aperture reinforcement backing 278 for use in forming the apertures 233A, 233B, 235A, 235B in the elbow brace 220 of FIGS. 5A-5B.

There are various possibilities with regard to alternative embodiments of a elbow brace according to the invention.

Although in a preferred embodiment the elbow brace includes a base which is formed as a reclosable sleeve made from a sheet of elastic material, this is not required. The elastic material could be a single material, it could be woven or no-woven, it could be a coated material, or a sandwich of materials. For example, the base may also be formed of a tubular elastic sleeve shaped to fit snugly about the elbow. The base may include an opening to receive the point of the elbow to align the base on the limb of the wearer, and this opening, if present, could have a variety of shapes, e.g. circular, square, rectangular, elliptical, diamond, trapezoidal, or any substantial equivalent. All such alternative embodiments will be referred to herein as a base.

Although in a preferred embodiment the lateral sides of the base each terminate in upper and lower fastening straps, with a side recess between the upper and lower fastening straps, this is not required. For example, the sides of the base, or portions thereof, could be straight.

Although in a preferred embodiment the base is detachably fastened about the elbow, upper-arm, and forearm of the wearer using hook and loop material of the type which adheres when pressed together, this is not required. For example, other fasteners such as buttons, clasps, buckles, pins, zippers, straps, buttons or other substantial equivalents may be substituted for the hook and loop type fastener material.

Although in a preferred embodiment, various components are permanently fastened together using stitches, this is not required. For example, other means such as glue, thermal bonding, ultrasonic bonding, or other substantial equivalents could be used.

In elbow brace 120, the base 122 and tension member 124 can be made of the same elastomeric material, such as a coated polyurethane foam material bearing fabric loops that stretches primarily in a lengthwise direction. However, this construction is not required and other constructions and materials could be used. For example, the base could be made of a material that stretches primarily in a lengthwise direction, with a tension member made of a different material that stretches in multiple directions, for example of the type known as spandex in the United States or elasthane, or sold under the trademark LYCRA®.

In elbow brace 220, the tension member 224 may comprise an anchor portion permanently fastened to the base and made of a material that stretches in multiple directions (for example spandex), along with separate strap portions made of a material bearing fabric loops that stretches primarily in a lengthwise direction. However, this construction is not required and other constructions and materials could be used. For example, the material types could be swapped, with the anchor portion made of a material that stretches primarily lengthwise and the strap portions made of a material that stretches in multiple directions.

Alternatively, the tension member 224 could have a unitary construction made of a single material (except for fastening tabs 266) that forms both the anchor portion and the strap portions. If a unitary construction is used, the single material could be either a material that stretches in multiple directions (for example spandex) or a material bearing fabric loops that stretches primarily in a lengthwise direction (for example a coated polyurethane foam).

Advantageously, the external surface of the rear of an elbow brace according to the invention does not bear any structure, and can be smooth except for any stitches that secure the tension member to the inside of the base. The smooth external surface can be maintained, for example to provide an attractive and clean appearance that will not snag or obstruct motion during use. Alternatively other structures such as thick elbow pads for use in contact sports like football or hockey could be positioned on the external surface for particular applications.

It is understood that the invention is not confined to the embodiments set forth herein as illustrative, but embraces all such forms thereof that come within the scope of the following claims.

What is claimed is:
1. An elbow brace, comprising:
 (a) a base wearable in snug covering relationship to portions of an elbow and adjacent portions of an upper-arm and forearm of a person, the base having an exterior surface and an interior surface when worn; and
 (b) a tension member having a first upper tensioning strap, a second upper tensioning strap, a first lower tensioning strap, and a second lower tensioning strap, wherein the tension member is positioned between the base and the arm of the person when worn;

wherein the base includes a first upper aperture, a second upper aperture, a first lower aperture, and a second lower aperture;

and wherein the first upper tensioning strap extends through the first upper aperture, wherein the second upper tensioning strap extends through the second upper aperture, wherein the first lower tensioning strap extends through the first lower aperture, and wherein the second lower tensioning strap extends through the second lower aperture when the brace is worn;

wherein at least a portion of the exterior surface of the base bears loop-type material, and wherein each of the first upper tensioning strap, the second upper tensioning strap, the first lower tensioning strap, and the second lower tensioning strap has a free end bearing a hook-type material, whereby the free ends of the tensioning straps may be detachably attached to the exterior surface of the base.

2. The elbow brace of claim 1 wherein the base has a base central portion mid-line axis, wherein the tension member has a tension member central portion mid-line axis, and wherein the tension member is permanently fastened to the base by a plurality of stitches through at least a portion of the base central portion mid-line axis and through at least a portion of the tension member central portion mid-line axis.

3. The elbow brace of claim 2 wherein the tension member is not otherwise permanently attached to the base.

4. The elbow brace of claim 1 wherein the tension member is formed of a material which stretches in multiple directions, and the base is formed of a material which stretches primarily in a single direction.

* * * * *